(12) United States Patent
Hamakubo et al.

(10) Patent No.: US 7,070,978 B2
(45) Date of Patent: Jul. 4, 2006

(54) METHOD FOR EXPRESSING AND PURIFYING PROTEINS USING BUDDED BACULOVIRUS

(75) Inventors: Takao Hamakubo, Tokyo (JP); Tatsuhiko Kodama, Tokyo (JP); Mineko Yamaguchi, Tokyo (JP)

(73) Assignee: Toudai TLO, Ltd., Tokyo (JP)

( * ) Notice: Subject to any disclaimer, the term of this patent is extended or adjusted under 35 U.S.C. 154(b) by 33 days.

(21) Appl. No.: 09/884,481

(22) Filed: Jun. 20, 2001

(65) Prior Publication Data

US 2003/0027131 A1  Feb. 6, 2003

(51) Int. Cl.
*C12N 7/02* (2006.01)
*C12N 15/86* (2006.01)
*C12N 15/09* (2006.01)

(52) U.S. Cl. .................. 435/239; 435/456; 435/69.7
(58) Field of Classification Search ............. 435/320.1, 435/325, 7.2, 41, 69.1, 69.2, 70.1, 70.2, 5, 435/71.1, 235.1, 239; 530/344
See application file for complete search history.

(56) References Cited

U.S. PATENT DOCUMENTS 5,858,750 A * 1/1999 Bandman et al. ............ 435/190
2002/0052040 A1  5/2002 Hunt ........................... 435/235

FOREIGN PATENT DOCUMENTS

WO    98/46777    10/1998
WO    01/02551    1/2001

OTHER PUBLICATIONS

Ikeda et al. PNAS. 1995; 92: 126-130.*
Loisel et al. Nature Biotechnology. Nov. 1997; 15: 1300-1304.*
Grabherr et al. Biotechniques. 1997; 22 (4): 730-735.*
Boublik et al. Biotechnology. Oct. 1995; 13: 1079-1084.*
Possee. Current Opinion in Biotechnology. 1997; 8: 569-572.*
Nohtureflt et al. PNAS. 1999; 96: 11235-11240.*
Duncan et al. Journal of Biological Chemistry. 1997; 272 (19): 12778-12785.*
Fields, Virology, Third Edition, vol. 1, p. 539.*
Lanford et al., "Expression and Characterization of Hepatitis B Virus Surface Antigen Polypeptides in Insect Cells with a Baculavirus Expression System," Journal of Virology, vol. 63, No. 4; pp. 1549-1557 (1989).*

* cited by examiner

*Primary Examiner*—James Housel
*Assistant Examiner*—M. Franco Salvoza
(74) *Attorney, Agent, or Firm*—Greenblum & Bernstein P.L.C.

(57) ABSTRACT

Method for efficiently expressing a protein in an active form by using baculovirus expression system wherein the protein is selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein. There is provided a method for expressing such a protein by culturing a host infected with at least one type of recombinant baculovirus which contains a gene encoding the protein, wherein the protein is expressed in a budded baculovirus released from the host.

22 Claims, 9 Drawing Sheets

Expression of SREBP2 in Sf9 cells

CBB staining

Immunoblot staining with anti-SREBP2

Fig.1 Expression of SREBP2 in Sf9 cells

Fig.2 Centrifugation separation of SREBP2 expressed in culture supernatant

Lane 1   800 g    10 min   Supernatant
Lane 2   40000 g  20 min   Supernatant
Lane 3   40000 g  20 min   pellet Fig.3 Density gradient centrifugation of 40000g pellet Fig. 4  Solubilization and Purification of SREBP from Budded virus Immunoblot with anti-SREBP
Lane 1:     Solubilized SREBP
Lane 2, 3:  Affinity column pass through
Lane 4, 5:  10M urea eluate from affinity column
Lane 6:     PD10 gel filtration Fig.5　Preparation of mouse anti-serum Fig.6    Expression of S1P in Budded virus

S1P recombinant virus

48h  72h  80h  96h  Wild

216 →
132 →
 ▶
78 →

46 →

Immunoblot with anti-S1P serum.
Arrow head; S1P

Fig. 7 Cleavage of SREBP on BV by S1P on BV

Immunoblot analysis with R004 (anti- N-terminal Domain of SREBP)

lane 1 : SREBP (preincubation)
2 : SREBP
3 : SREBP + S1P
4 : SREBP + S1P + 5 mM Ca
5 : SREBP + S1P + 10 mM EGTA
6 : SREBP + S1P + 10 mM EDTA
7 : S1P lane 2 - 7: Samples were incubated at 37°C for 12 hr.

SREBP ↓
← 78 K
← 64 K (kDa)
205 →
120 →
84 →
52.2 →
36.3 →

8% SDS-PAGE

Fig.8   Expression of SCAP in budded virus

Immunoblot with anti-His Tag

Fig. 9 Coexpression of SREBP2 and SCAP

US 7,070,978 B2

METHOD FOR EXPRESSING AND PURIFYING PROTEINS USING BUDDED BACULOVIRUS

TECHNICAL FIELD TO WHICH THE INVENTION BELONGS

The present invention relates to a technology for expressing a protein present on a membrane such as an endoplasmic reticulum membrane or a Golgi apparatus membrane using a baculovirus expression system. More particularly, the present invention relates to a method for expressing a membrane protein in a budded baculovirus by culturing a host infected with at least one type of recombinant baculovirus which contains a gene encoding the membrane protein.

BACKGROUND OF THE INVENTION

A baculovirus expression system enables high-level expression of a gene of interest by causing recombination of the gene in Sf9 cells using a promoter of a polyhedrin gene of baculovirus. A polyhedrin is expressed in the nucleus of Sf9 cell at a high level as an occlusion body which is a form to be used when viruses become latent within the cell. The baculovirus expression system where a recombinant protein is introduced into a polyhedrin gene and the expressed proteins are purified, has many advantages over that of *Escherichia coli*, such that the expressed proteins are hard to agglutinate and the expressed proteins undergo a posttranscriptional modification which is necessary for protein functions, such as addition of sugar chains and coordination of metal ion.

Baculovirus has another life cycle. In order to proliferate and infect, baculovirus becomes a budded virus (Budded virus: this is also referred to as budded baculovirus in this specification), rupturing Sf9 cell membrane and being released outside the cell. Bouvier et al have reported that at this time a receptor of seven-transmembrane type recombined into the above polyhedrin protein is expressed on the cell membrane and recovered from the envelope of the budded baculovirus (Loisel T P, Ansanay H, St-Onge S, Gay B, Boulanger P, Strosberg A D, Marullo S, Bouvier M., Nat Biotechnol. 1997 November; 15(12): 1300–4., Recovery of homogeneous and functional beta 2-adrenergic receptors from extracellular baculovirus particles; and International Publication WO98/46777). It has also been reported that, whereas most receptors of seven-transmembrane type expressed in a host cell have a sugar chain structure which is not functional, only functional receptors are recovered from the viral envelope. However, Bouvier et al have not mentioned membrane proteins other than receptor proteins.

SUMMARY OF THE INVENTION

A problem to be solved by the present invention is to provide a method for efficiently expressing a protein in an active form by using baculovirus expression system wherein the protein is selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein. Another problem to be solved by the present invention is to provide a method for producing antibodies against the above expressed proteins by using the above method, and a method for screening a chemical substance useful as drugs and the like by using the above method.

SREBP (sterol regulatory element binding protein) 2, HMG-CoA (hydroxymethylglutaryl coenzyme A) reductase, SCAP (SREBP cleavage activating protein), and S1P (site 1 protease) are of a membrane protein group which is distributed over the endoplasmic reticulum (ER) membrane or the Golgi apparatus membrane, and is involved in intracellular cholesterol feedback regulation. The present inventors have succeeded in recovering these proteins from extracellular budded viral envelopes by allowing Sf9 cells to express these proteins using a baculovirus expression system. It was also found that an ER membrane protein recovered from the viral envelope forms a single band and has a higher stability as compared to a membrane protein recovered from Sf9 cell membrane with many degradation products. The present invention have been completed based on these findings.

According to the present invention, there is provided a method for expressing a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein by culturing a host infected with at least one type of recombinant baculovirus which contains a gene encoding said protein, wherein said protein is expressed in a budded baculovirus released from said host.

According another aspect of the present invention, there is provided a method for preparing a protein which comprises:

culturing a host infected with a recombinant baculovirus which contains a gene encoding a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein;

recovering a budded baculovirus released from said host; and recovering the protein expressed from said budded baculovirus.

Preferably, the protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein is a membrane-bound protein of a cell organelle.

Preferably, the protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein is SREBP2, HMG-CoA reductase, S1P, or SREBP cleavage activating protein.

Preferably, the host is an insect cell or an insect larva.

According to further another aspect of the present invention, there is provided a budded baculovirus which is released from a host infected with at least one type of baculovirus which contains a gene encoding a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein.

According to still further another aspect of the present invention, there is provided a method for screening a chemical substance which comprises measuring interaction between said protein and other chemical substances using the budded baculovirus of the present invention.

Preferably in the present invention, a drug which inhibits or activates a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein, is screened.

According to still further another aspect of the present invention, there is provided a method for screening a chemical substance which activates or inhibits the function of two or more proteins selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein, by co-infecting two or more different types of recombinant baculoviruses, each of which contains a gene encoding a different type of said protein; and co-expressing the function of said two or more proteins.

According to still further another aspect of the present invention, there is provided a method for producing an antibody against a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein, wherein the budded baculovirus of the present invention is used as an immunogen, as well as an antibody which is produced by this method.

In one aspect, the present invention is directed to a method for recovering a budded baculovirus expressing an intracellular organelle membrane-bound protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein comprising culturing a host infected with at least one recombinant baculovirus which contains a gene encoding said protein, expressing said protein in said infected host allowing baculovirus produced in said host to bud and be released from said host with said expressed protein being in the envelope of said budded baculovirus, and separating the budded baculovirus.

In another aspect, the present invention is directed to a method for preparing an intracellular organelle membrane-bound protein which comprises culturing a host infected with a recombinant baculovirus which contains a gene encoding a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein; recovering a budded baculovirus released from said host; and recovering the protein expressed in said infected host allowing baculovirus produced in said host to bud and be released from said host with said expressed protein being in the envelope of said budded baculovirus.

In still another aspect, the present invention is also directed to a method for recovering a budded baculovirus expressing a non-receptor protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein comprising culturing a host infected with at least one recombinant baculovirus which contains a gene encoding said protein, expressing said protein in said infected host allowing baculovirus produced in said host to bud and be released from said host with said expressed protein being in the envelope of said budded baculovirus, and separating the budded baculovirus.

In still another aspect, the present invention is directed to a method for preparing a non-receptor protein which comprises culturing a host infected with a recombinant baculovirus which contains a gene encoding a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein; recovering a budded baculovirus released from said host; and recovering the protein expressed in said infected host allowing baculovirus produced in said host to bud and be released from said host with said expressed protein being in the envelope of said budded baculovirus.

DETAILED DESCRIPTION OF THE INVENTION

The embodiments and methods of the present invention will be described below in detail.

The method of the present invention relates to a method for expressing a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein by culturing a host infected with at least one type of recombinant baculovirus which contains a gene encoding the protein, wherein the protein is expressed in budded baculovirus which is released from the host.

The term "membrane-bound" as used herein broadly means that a protein exists in cell membrane or in the membrane of intracellular organelle (e.g. endoplasmic reticulum or Golgi apparatus), and the type of the proteins is not specifically limited. Preferably, a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein, is a membrane-bound proteins of intracellular organelles such as proteins bound to the membranes of endoplasmic reticulum and of Golgi apparatus.

Membrane-bound enzymes include, for example, HMG-CoA reductase involved in cholesterol metabolism, ACAT (acyl-coenzyme A: cholesterol acyltransferase), and 7. -hydroxylase. Other examples are the cytochrome P450 system involved in detoxification, ATP synthase present in mitochondria, cytochrome oxidase and reductase, and electron transport system enzymes such as NADH-Q reductase. Still other examples include: a processing protease family involved in processing of hormones, controlling factors, nutritional factors and the like, such as S1P (site 1 protease), furin, PC (proprotein convertase), S2P (site 2 protease), endothelin converting enzyme, angiotensin converting enzyme, and neprilysin; an ADAMS (a disintegrin and metalloprotease) family which is involved in signal transduction system such as notch signal; β-selectase and γ-selectase which cleave amyloid precursor proteins (e.g. presenillin); and a matrix metalloprotease family which is involved in the decomposition of the extracellular matrix. Other examples are membrane lipid metabolizing enzymes such as diacylglycerol synthase, phosphatidic acid phosphatase, and phosphatidylserine synthase; and enzymes involved in signal transduction such as adenylate cyclase.

Examples of membrane-bound enzyme-substrate proteins include those involved in signal transduction and transcriptional control, such as sterol regulatory proteins (SREBP), Notch, Ire1, and ATF6, and other amyloid precursor proteins, TNF. (tumor necrosis factor) precursor, Stem cell factor, M-CSF (monocyte colony stimulating factor) precursor, and Klotho.

Examples of membrane-bound enzyme activators include presenillin, and SCAP (SREBP cleavage activating protein).

Examples of membrane-bound transport proteins include NPC (Niemann-Pick type c) 1 which transport lipid such as cholesterol, ABC (ATP-binding cassette) transporter, caveolin and fatty acid transporter; as well as sugar transporters including glucose transporters such as GLUT1-4 and amino acid transporters such as glutamate transporter and serotonin transporters. Examples of membrane proteins involved in a transportation of a substance between intracellular vesicles include Sec12.

Other examples are channel proteins which allow selective passage of membrane impermeable molecules under certain condition. Such channel proteins include aquaporin family which is selective channels for water, and ion channels which are selective channels for potassium ions, calcium ions, sodium ions and the like.

Examples of membrane structural proteins and proteins involved in adhesion include NCAM (Neural cell adhesion molecule), ICAM (intercellular adhesion molecule), the cadherin family, integrin, desmocholine, desmograin, L-selectin, connexin, and glycoproteins. Other examples include major histocompatibility complex (MHC) involved in antigen presentation in immunocytes, and chaperone proteins such as calnexin, PDI (protein disulfide isomerase), CFTR (cystic fibrosis transmembrane conductance regulator), and major prion protein precursor (prion), which are thought to be involved in the formation of high dimensional structure of a protein.

From the above, it is apparent that the proteins according to the present invention include intracellular organelle proteins and/or non-receptor proteins.

In the present invention, at least one type of recombinant baculovirus containing a gene encoding the above-mentioned protein to be expressed is employed.

Baculoviruses which infect insects and cause diseases are envelope viruses having cyclic double stranded DNAs as gene, and shows a sensitivity to insects of the orders Lepidoptera, Hymenoptera, Diptera and the like. Among the baculoviruses, nuclear polyhedrosis virus (NPV) refers to a group which produces a large amount of occlusion bodies called polyhedra within the nucleus of an infected cell. A polyhedron comprises polyhedrin proteins having a molecular weight of 31 kDa, and is produced in a large amount at late stage of the infection and have many viral particles embedded therein. Since polyhedra is essential for the viruses to survive in nature, but unnecessary for the proliferation of a virus, the viruses can infect and proliferate even if a foreign gene to be expressed is inserted in place of a polyhedron gene.

As baculoviruses used in the present invention, a virus vector such as *Autographa californica* NPV (AcNPV) of the subfamily Phytometra and *Bombyx mori* NPV (BmNPV) of silkworm, can be used.

Example of a host of AcNPV (infected and established cells) include *Spodoptera frugiperda* cell (Sf cell), and that of BmNPV (infected and established cells) include BmN4 cell. Vectors of AcNPV line are preferred because Sf cell possesses a higher proliferation rate compared to BmN4 cells and the like, and AcNPV possesses infectivity to human liver cells, human fetal nephrocytes and the like.

As hosts, for example, *Spodoptera Frugiperda* cell lines Sf9 and Sf21 have been established from ovarian tissue of *S. frugiperda* larva and are available from Invitrogen, Pharmingen (San Diego, Calif.), ATCC or the like. In addition, a living insect larva can also be used as a host.

A method for constructing a recombinant virus used in the present invention may be performed by standard techniques, and it can be performed by, for example, the following steps.

First, a recombinant transfer vector is constructed by inserting a gene of a protein to be expressed into the transfer vector.

The whole size of the transfer vector generally ranges from about several kb to about 10 kb where about 3 kb of the size corresponds to a backbone derived from a plasmid, which contains an antibiotic resistance gene (e.g. resistance to ampicillin) and a signal to initiate DNA replication in bacteria. In addition to this backbone, a transfer vector generally contains several kb each of the 5' and 3' regions of a polyhedron gene, so that, when transfection as described below is performed, homologous recombination between the gene of interest and the polyhedron gene occurs between these sequences. Preferably, the transfer vector contains a promoter for the expression of a gene of a protein. Examples of promoters include a polyhedron gene promoter, a p10 gene promoter, and a capsid gene promoter.

Types of transfer vectors are not specifically limited. Examples of AcNPV line transfer vectors include pEVmXIV2, pAcSG1, pVL1392/1393, pAcMP2/3, pAcJP1, pAcUW21, pAcDZ1, pBlueBacIII, pAcUW51, pAcAB3, pAc360, pBlueBacHis, pVT-Bac33, pAcUW1, and pAcUW42/43; those of BmNPV line transfer vectors include pBK283, pBK5, pBB30, pBE1, pBE2, pBK3, pBK52, pBKblue, pBKblue2, pBF series (all of which are available from FUNAKOSHI, Fujisawa Pharmaceutical Co., Ltd. and the like).

Next, in order to prepare recombinant viruses, the above-mentioned recombinant transfer vectors are mixed with viruses, and then transferred into cultured cells to be used as a host, or alternatively are transferred into cultured cells to be used as host which have been previously infected with viruses, so as to cause homologous recombination between the recombinant transfer vectors and viral genome DNAs, thereby constructing recombinant viruses.

Cultured cells used as a host are the above-mentioned host, and generally include insect culture cells (e.g. Sf9 cells, BmN cells, etc.). Culturing conditions are determined appropriately by persons skilled in the art. When Sf9 cells are used, culturing is preferably performed at around 28° C. in a medium containing 10% fetal calf serum. The thus constructed recombinant viruses can be purified by standard techniques such as plaque assay. The thus prepared recombinant viruses can be easily distinguished from non-recombinant viruses since they cannot form polyhedra because of the foreign DNA replaced or inserted in the region of the gene for the polyhedron protein of the nuclear polyhedrosis virus.

In the method of the present invention, the protein of interest can be recovered by allowing the above-mentioned recombinant baculovirus to infect the above-described appropriate host (culture cells of e.g. *Spodoptera Frugiperda* cell lines Sf9 and Sf21 or insect larvae) and recovering extracellular budded virus (BV) from the culture supernatant by separation means such as centrifugation after a certain period of time (e.g. 72 hours). Only one type of recombinant baculovirus may be infected, or two or more types of recombinant baculovirus may be co-infected.

Extracellular budded baculoviruses can be recovered, for example, as described below.

First, a culture solution of the infected cells is centrifuged at 500 to 1,000 g, thereby recovering the supernatant containing extracellular budded baculoviruses. The supernatant is centrifuged at about 30,000 to 50,000 g so as to obtain the precipitate containing extracellular budded baculoviruses. The precipitate is suspended in an appropriate buffer. The virus suspension is applied onto proper concentration gradients (e.g. sucrose sequential gradient), and then centrifuged at 100,000 g for fractionation. Finally, fractions containing desired proteins can be selected from the obtained fractions.

When the expressed proteins are obtained in the form of solubilized proteins, extracellular budded viruses are recovered by centrifugation at e.g. 40000 g from the culture solution of the infected cells. The recovered pellet is suspended in an appropriate buffer, treated with a dissolution agent such as lyso-phosphatidylcholine, and centrifuged at 30,000 rpm, thereby separating the suspension into a supernatant and a precipitate. The solubilized protein of interest is recovered in the supernatant.

The expressed protein recovered by the method of the present invention as described above is characterized in that it is recovered in its active form. Preferably, at least 50% or more, more preferably 60% or more, still more preferably 70% or more, further more preferably 80% or more, still more preferably 90% or more, and particularly preferably 95% or more of the protein is recovered in its active form by the method of the present invention. Such an active form of a membrane protein could not be recovered in a high yield by the conventional methods.

The present invention further provides a method for screening a chemical substance which comprises measuring interaction between other chemical substances and a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein, by using budded baculoviruses which are released from hosts infected with at least one type of recombinant baculovirus which contain a gene encoding said protein.

Examples of chemical substances to be screened include peptides, polypeptides, synthetic compounds, fermented products of microorganisms, extracts from organisms (including plant or animal tissues, microorganisms and cells) or libraries thereof. Examples of libraries include a synthetic compound library (e.g. a combinatorial library) and a peptide library (e.g. a combinatorial library). Chemical substances to be screened may be either natural or synthetic materials. Single candidate chemical substance may be individually tested, or a mixture of candidate chemical substances (including libraries) may be tested. Furthermore, a fractionated mixture such as a cell extract may be screened, followed by repeated fractionation, thereby isolating a substance with a desired activity.

These chemical substances are substances which are expected to interact with a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein. More preferably, these chemical substances are drugs which inhibit or activate the above-described proteins.

The present invention further provides a method for producing an antibody against a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein, which is characterized by using, as an immunogen, budded baculoviruses which are released by hosts infected with at least one type of recombinant baculoviruses that contains a gene encoding a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein.

The preparation of antibodies can be performed by standard techniques. When a polyclonal antibody is produced, mammals are immunized as antigens with budded baculoviruses which are released from hosts infected with at least one type of recombinant baculovirus which contains a gene encoding a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein; blood is collected from the mammals; and antibodies are separated and purified from the collected blood. Examples of mammals which can be immunized include mice, hamsters, guinea pigs, chickens, rats, rabbits, dogs, goats, sheep, and cattle. Immunization can be performed by standard immunization techniques, for example by administering antigens once or more.

Preferably, antigens are administered twice or three times at an interval of 7 to 30 days, particularly 12 to 16 days, and the dose may be appropriately selected. The route of administration is not specifically limited and can be appropriately selected from subcutaneous administration, intracutaneous administration, intraperitoneal administration, intravenous administration, and intramuscular administration. Administration by intravenous, intraperitoneal, or subcutaneous injection is preferred. The antigen may be dissolved in an appropriate buffer such as that which contains a generally employed adjuvant, such as complete Freund's adjuvant, RAS [MPL(Monophosphoryl Lipid A)+TDM(Synthetic Trehalose Dicorynomycolate)+CWS(Cell Wall Skeleton) adjuvant system], or aluminum hydroxide. The above adjuvant may not be used depending on the administration route and the conditions.

The immunized mammals are raised for e.g. 0.5 to 4 months, and a small amount of the sera of the mammals is sampled from vena of the ears, and then the antibody titer is measured. When the antibody titer is increasing, antigen is administered at appropriate frequency depending on the condition. For example, booster immunization is performed using 100 μg to 1000 μg of antigen. One to 2 months after the final administration, blood is collected by standard techniques from the immunized mammals. The collected blood is separated and purified by standard methods such as precipitation using centrifugation, ammonium sulfate or polyethylene glycol, and chromatography including gel filtration chromatography, ion exchange chromatography and affinity chromatography, thereby obtaining desired polyclonal antibodies as polyclonal anti-sera.

When a monoclonal antibody is produced, a desired monoclonal antibody can be obtained by producing a hybridoma by cell fusion of an antibody-producing cell and a myeloma cell line. A hybridoma producing a monoclonal antibody can be obtained by a cell fusion method as described below.

Spleen cells, lymph node cells, B lymphocytes and the like from immunized animals are used as antibody-producing cells. Extracellular budded baculoviruses are used as antigens. Animals to be immunized include mice and rats. Antigens are administered to these animals by standard techniques. For example, a suspension or emulsion is prepared from an adjuvant such as a complete Freund's adjuvant and incomplete Freund's adjuvant and budded baculoviruses as antigens. The preparation is administered for example intravenously, subcutaneously, intracutaneously or intraperitoneally to animals several times, thereby immunizing the animals. Next, for example, spleen cells are obtained as antibody-producing cells from the immunized animals, and are fused with myeloma cells by a known method (G. Kohler et al., Nature, 256 495 (1975)), so that hybridomas can be prepared. Examples of myeloma cell lines used for cell fusion include mouse P3X63Ag8, P3U1 strain, and Sp2/0 strain. In the cell fusion, a fusion accelerator such as polyethylene glycol and Sendai viruses is used. For selection of hybridomas after cell fusion, a HAT (hypoxanthine aminopterin thymidine) medium can be used according to standard techniques.

Hybridomas obtained by cell fusion are cloned by limiting dilution and the like, and further screened, thereby obtaining a cell line which produces a monoclonal antibody specifically recognizing a desired protein.

To produce a monoclonal antibody of interest from the thus obtained hybridoma, the hybridoma is cultured by a standard cell culturing method or an ascite formation method, and then the monoclonal antibody can be purified from the culture supernatant or the ascite. Purification of monoclonal antibodies from the culture supernatant or the ascite can be performed by standard techniques. For example, an appropriate combination of ammonium sulfate fractionation, gel filtration, ion exchange chromatography, affinity chromatography and the like may be employed.

The present invention will be further explained by the following examples, but the invention is not limited by these examples.

EXAMPLES

Example 1

Purification of Sterol Regulatory Protein (SREBP 2) and Production of Antiserum

SREBP 2 is a transcriptional factor which is involved in transcriptional control of key enzymes, such as LDL receptor and HMG-CoA reductase, which are involved in intracellular control of cholesterol (Brown M S, Goldstein J., Proc. Natl. Acad. Sci. U.S.A., 1999 September 28; 96(20): 11041–8, A proteolytic pathway that controls the cholesterol content of membranes, cells, and blood). A precursor protein of 125 kd is present as a protein of two-transmembrane type in the ER membrane. Cholesterol depletion within a cell causes SREBP 2 to separate from a transmembrane site by two steps of cleavage by protease and to be released into the cytoplasm. Then, SREBP 2 migrates to the nucleus and activates transcription by binding to a sre sequence on the promoter of a cholesterol controlling gene (Brown M S, Goldstein J., Proc. Natl. Acad. Sci. U.S.A. 1999 September 28; 96(20): 11041–8, A proteolytic pathway that controls the cholesterol content of membranes, cells, and blood).

(1) Preparation of Recombinant Baculoviruses and Sf9 Cell Culture

A human SREBP 2 full length gene (Hua X, Yokoyama C, Wu J, Briggs M R, Brown M S, Goldstein J L, Wang X., Proc. Natl. Acad. Sci. U.S.A. 1993 December 15; 90(24): 11603–7., SREBP-2, a second basic-helix-loop-helix-leucine zipper protein that stimulates transcription by binding to a sterol regulatory element) was integrated into a pBlueBac™ vector (Invitrogen, Carlsbad, Calif.). Sf9 cells (Invitrogen) were sub-cultured in Grace's supplemented media (GIBCO BRL) containing 10% fetal calf serum (Sigma), penicillin (100 units/ml) and streptomycin (100 µg/ml) at 27° C. on a 10 cm diameter dish. Large scale culturing was performed in a 1L Spinner flask (Wheaton) with addition of 0.001% pluronic F-68 (GIBCO BRL). Recombinant baculoviruses were prepared according to the instructions (Bac-N-Blue™ Transfection Kit, Invitrogen). Recombinant baculoviruses were prepared by co-infecting Sf9 cells with Bac-N-Blue DNA (derived from ApMNPV) and 4 µg of pBlueBac-SREBP2.

(2) SDS-PAGE and Western Blot Analysis for Expression $0.83 \times 10^6$ cells/well of Sf9 cells were infected with the recombinant viruses prepared in (1) at MOI (multiplicity of infection) 5 in a 6-well dish. The cells and culture supernatant were collected periodically (24, 48, and 72 hours). After culturing for a certain period, Sf9 cells were scraped off with a cell scraper and centrifuged at 800 g for 10 minutes, thereby obtaining the cell fraction as a precipitate. The supernatant was stored as a culture supernatant fraction at $-70°$ C. until sample preparation. The cell fraction was suspended in 100 µl/well of an isotonic phosphate buffer (a phosphate buffered saline containing 0.1% Triton X-100, aprotinin 0.5 µg/ml, leupeptin 0.5 µg/ml, pepstatin A 1 µg/ml), and then added with 100 µg/ml PMSF (phenylmethylsulfonyl fluoride). After vortex at 4° C. for 30 minutes and centrifugation at 1000 g for 10 minutes, 20 µl of 5×SDS sample buffer (0.24M Tris-HCl, pH6.8, 2.25% β-mercaptoethanol, 2.25% SDS, 50% glycerol, and 0.0015% bromophenol blue) was added to 80 µl of the supernatant, followed by heat treatment at 95° C. for 10 minutes. To 80 µl of the culture supernatant fraction was added 20 µl of a 5×SDS sample buffer, and the mixture was subjected to heat treatment.

These samples were subjected to gel electrophoresis on 8% SDS-PAGE and then transferred to a nitrocellulose membrane (Highbond ECL, Amersham) at 50V for 2 hours. After blocking with blockase for 30 minutes, the transfer membrane was allowed to react at room temperature for 1 hour with a 3000-fold diluted mouse ascite authentic sample of monoclonal antibody 1C6 (ATCC No CRL-2224) which recognizes the carboxyl end of SREBP 2. Then, the membrane was washed three times with TBS (20 mM Tris-buffered saline, pH 7.4), allowed to react with a peroxidase-bound anti-mouse IgG antibody (Sigma) for 1 hour, and washed with TBS. The membrane was then allowed to chemically emit with Supersignal west dura (Pierce), exposing to X-ray film.

(3) Sf9 Large Scale Suspension Culture and Sucrose Density Gradient Centrifugation of Budded Viruses Sf9 cells were added at a concentration of $5 \times 10^8$ cells/500 ml in a Grace's supplemented medium containing 10% FCS, 0.001% PluronicF-68 (Gibco) in 1L spinner flask, and the cells were infected with SREBP 2 recombinant viruses at MOI 5 and cultured for 72 hours. The cells were removed by centrifugation at 800 g for 10 minutes, and the supernatant was ultra-centrifuged at 40,000 g for 20 minutes. The precipitate was suspended in 4 ml of a TE buffer (10 mM Tris, 1 mM EDTA, pH 7.4). 36 ml of a sequential sucrose gradient of 25% to 56% was prepared with TE buffer in tubes of a Beckman supercentrifuge SW28 rotor. The above virus suspension (1.2 ml) was placed onto the gradient, and centrifuged at 100,000 g for 90 minutes, and 1.5 ml fractions was collected from the top end of each centrifuge tube.

(4) Solubilization of SREBP 2

500 ml of the Sf9 culture cell suspension ($1 \times 10^9$) was infected with SREBP2 recombinant viruses at MOI 5. 72 hours later, extracellular budded viruses (BV) were recovered by ultra-centrifugation at 40,000 g for 20 minutes. The pellet from the ultra-centrifugation was suspended in 4 ml of TBS, to which lyso-phosphatidylcholine (Sigma) was added to a concentration of 1%, followed by treatment at room temperature for 2 hours. The mixture was centrifuged at 30,000 rpm for 20 minutes with a Beckman rotor 90 Ti, so that a supernatant and a precipitate were separately recovered. The solubilized proteins are recovered in the supernatant.

(5) Affinity Chromatography 40 mg of IgG was purified from 4L of the culture supernatant of hybridomas (ATCC) secreting 1C6 with a Protein G column (Pharmacia), and was coupled to 8 ml of CNBr activated-sepharose (Pharmacia) to prepare a 1C6 affinity chromatography column.

The solubilized proteins recovered in the supernatant fraction were subjected to buffer exchange with buffer A (20 mM HEPES buffer containing 20 mM Octyl-glucose, pH7.4) using a PD10 column (Pharmacia), and then was applied to 2 ml of the above 1C6 affinity chromatography column, washed with buffer A containing 0.5M NaCl, and then eluted with buffer A containing 10M urea. The elution fraction was exchanged with buffer A using PD10 column again, and applied to a MonoS column (Pharmacia), followed by elution with a linear gradient of NaCl (0 to 0.5M) on Pharmacia SMART system.

(6) Expression of SREBP2

Figure 1:
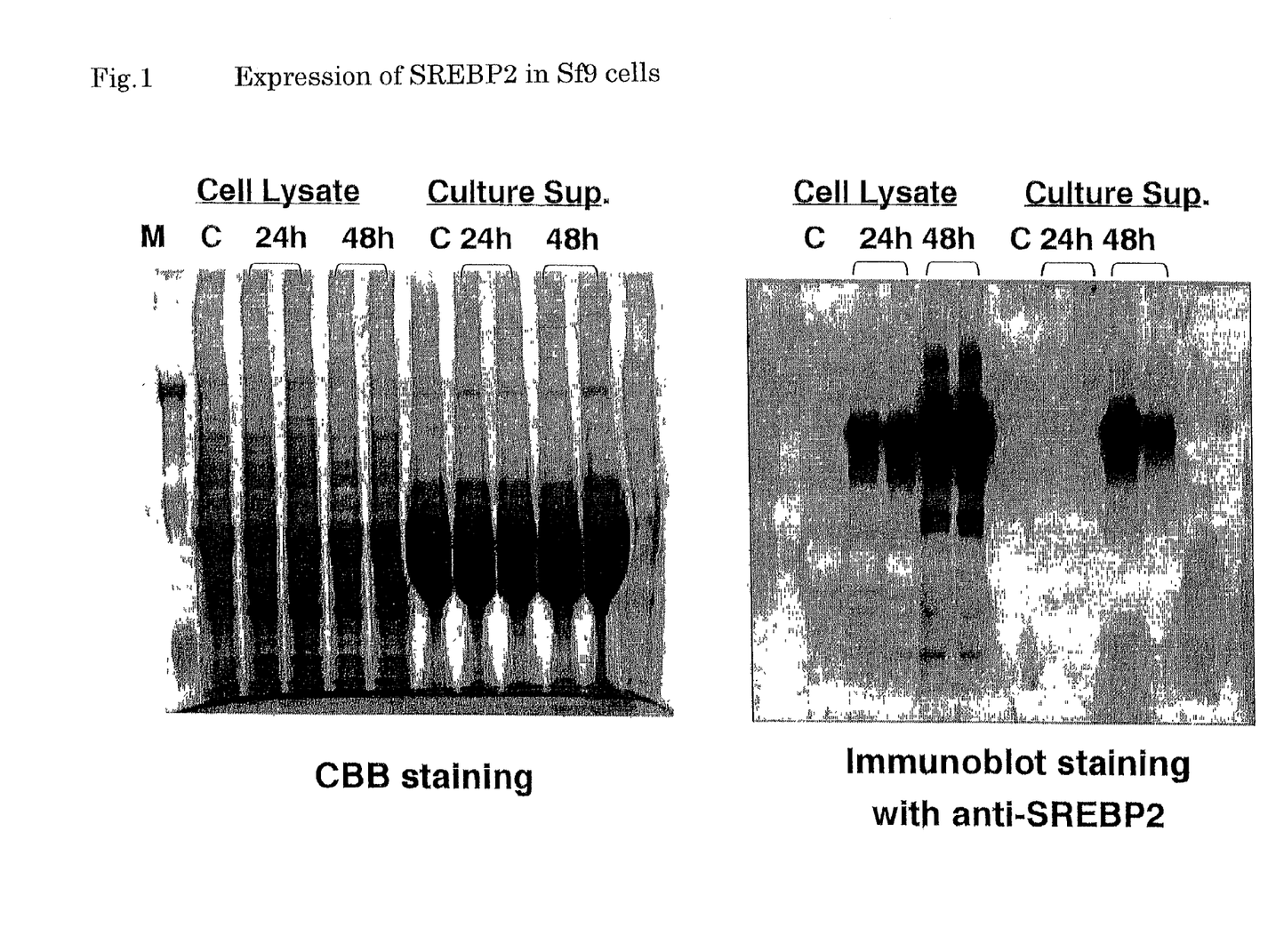
FIG. 1 is an illustration showing the expression of SREBP2 in Sf9 cells.
Figure 2:
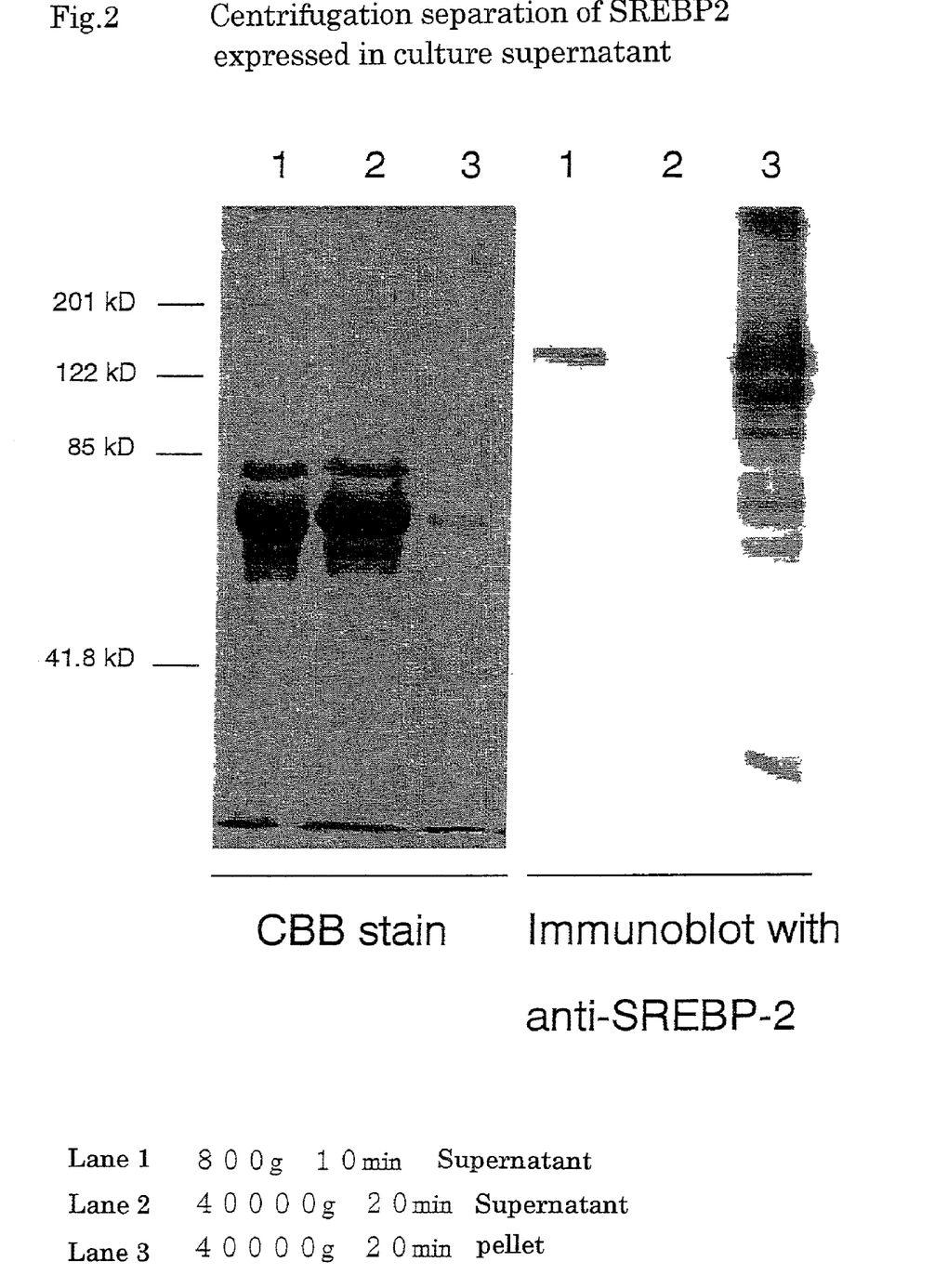
FIG. 2 is an illustration showing the result of centrifugation of SREBP2 expressed in the culture supernatant.
Figure 3:
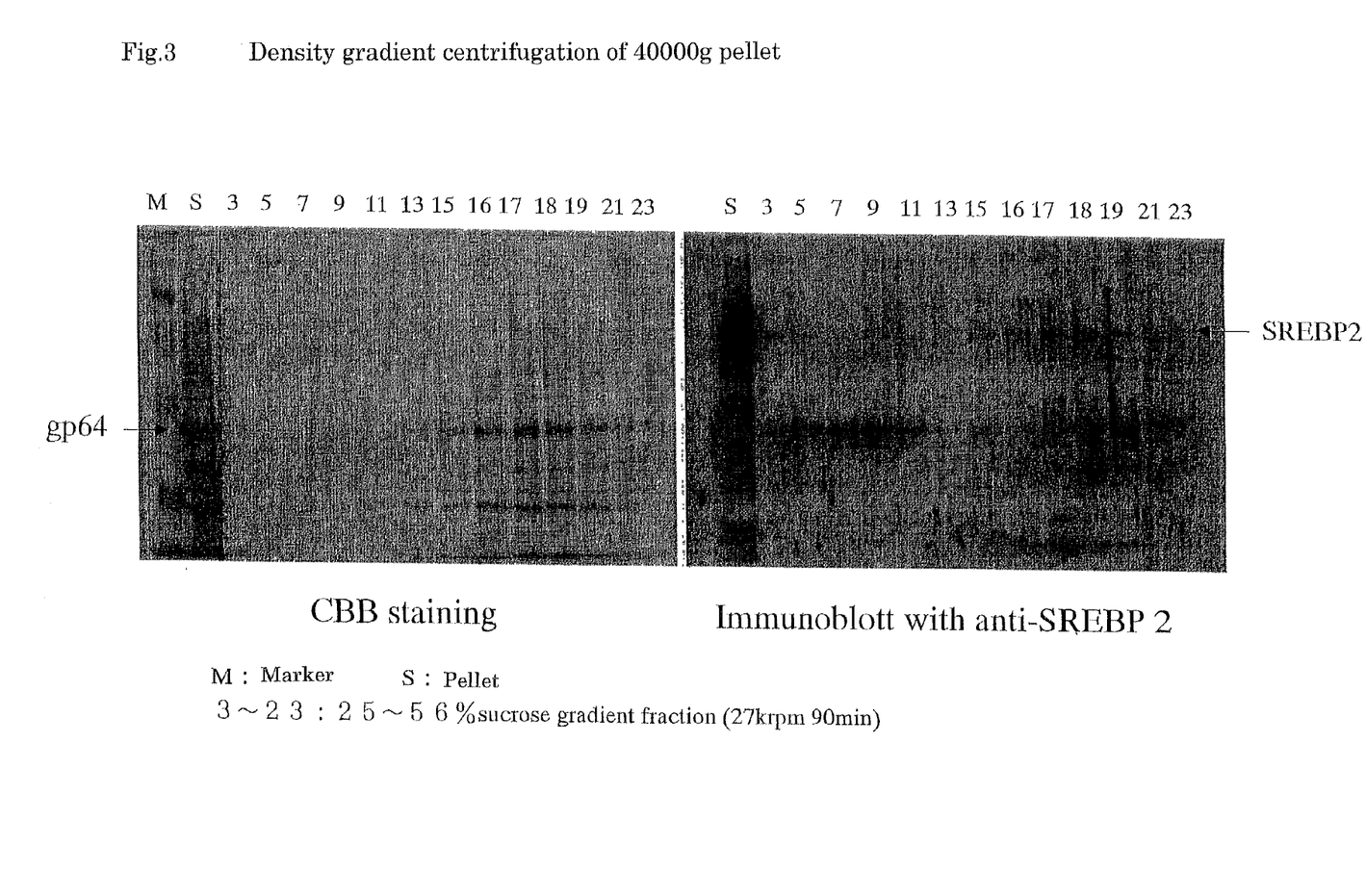
FIG. 3 is an illustration showing the result of density-gradient centrifugation of 40,000 g pellet.

The amount of expression was confirmed by Western blot using a monoclonal antibody 1C6 (ATCC, USA) which recognizes the carboxyl end (FIG. 1). As a result, expression was confirmed in Sf9 cells 24 hours after reaction and in the culture supernatant 48 hours after reaction. To confirm the source of SREBP2 which has been recovered in the culture supernatant 48 hours after reaction, the culture supernatant was centrifuged. SREBP2 was recovered in the supernatant by centrifugation at 800 g for 30 minutes, and recovered in the pellet fraction by centrifugation at 40,000 g for 20 minutes (FIG. 2). These results suggest that SREBP2 present in the culture supernatant is not debris such as dead cells, but is derived from membrane or extracellular virus. Further, when the pellet fraction was fractionated by sucrose density gradient centrifugation, SREBP2 protein was recovered in the same fraction as that of the virus envelope protein gp64 which is confirmed by SDS-PAGE with Coomassie staining (FIG. 3). This result suggests that SREBP2 is not debris of cell membranes, but is expressed in the virus.

Figure 4:
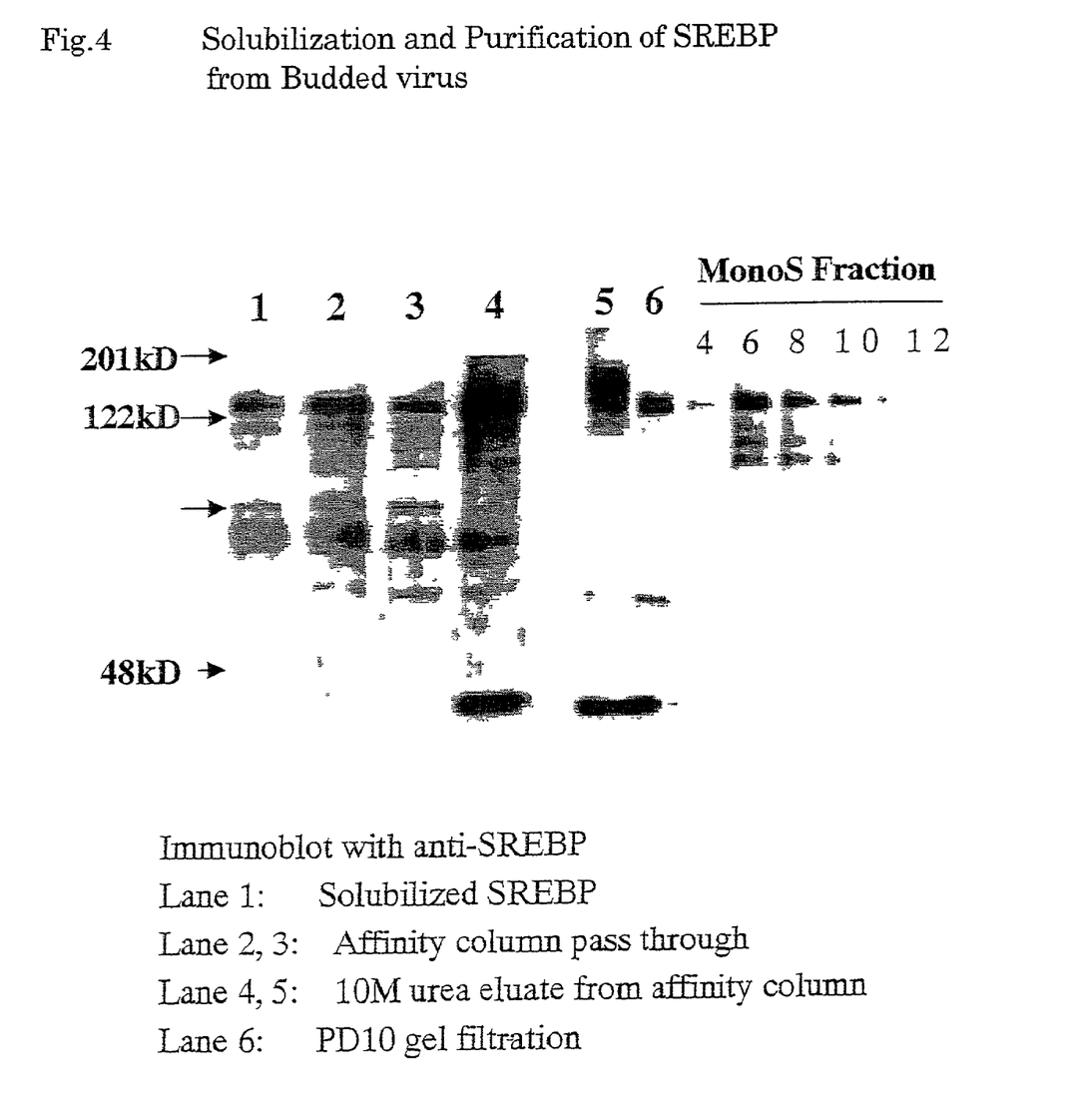
FIG. 4 is an illustration showing the results of solubilization and purification of SREBP from the budded virus.

Moreover, when the fraction was treated with 1% lysolecithin, approximately 80% of SREBP2 was recovered in the soluble fraction. SREBP2 can be purified by a 1C6 affinity column in which the antibody 1C6 has been coupled to CNBr sepharose (FIG. 4).

Figure 5:
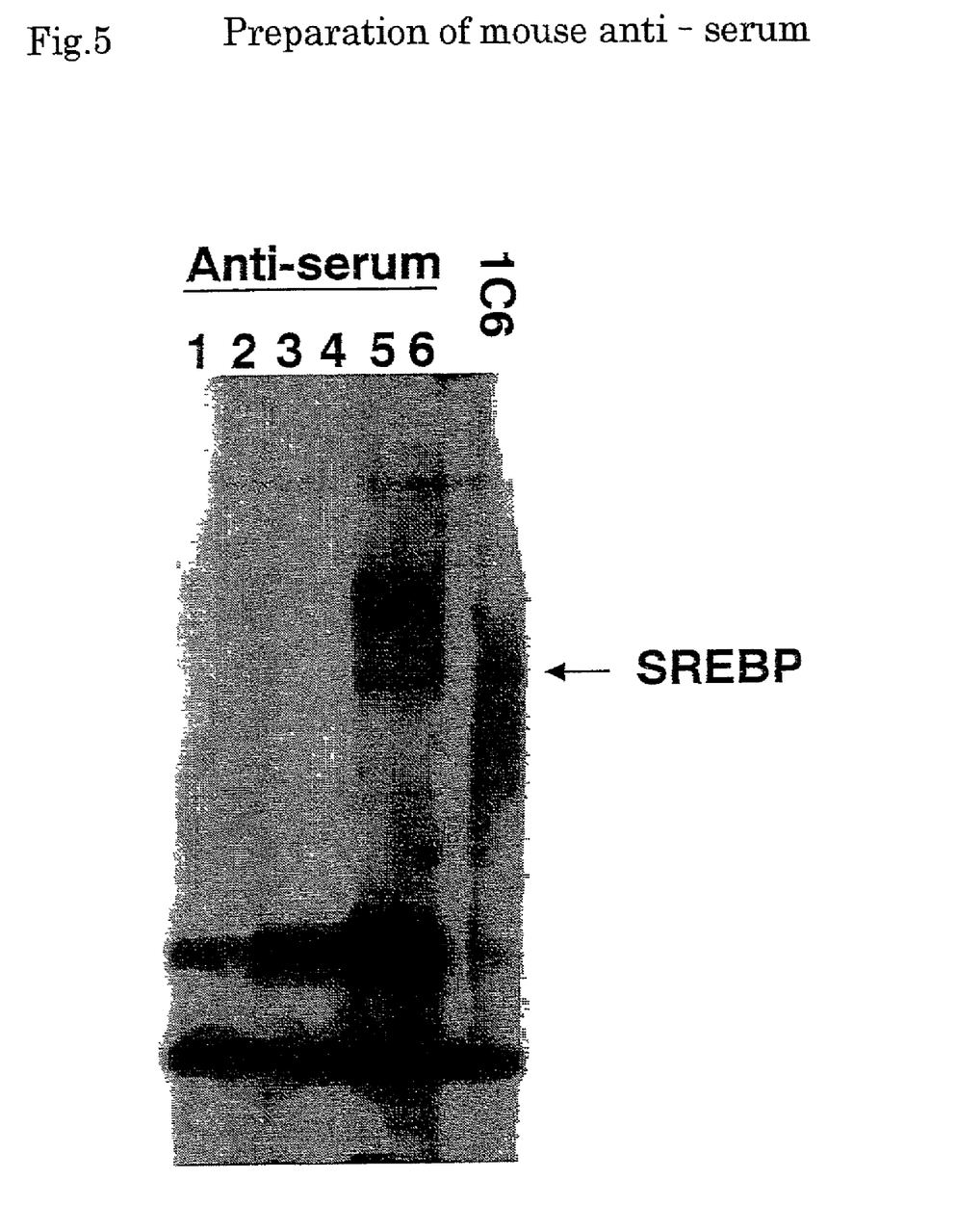
FIG. 5 is an illustration showing the result of production of a mouse anti-serum against SREBP.
Figure 6:
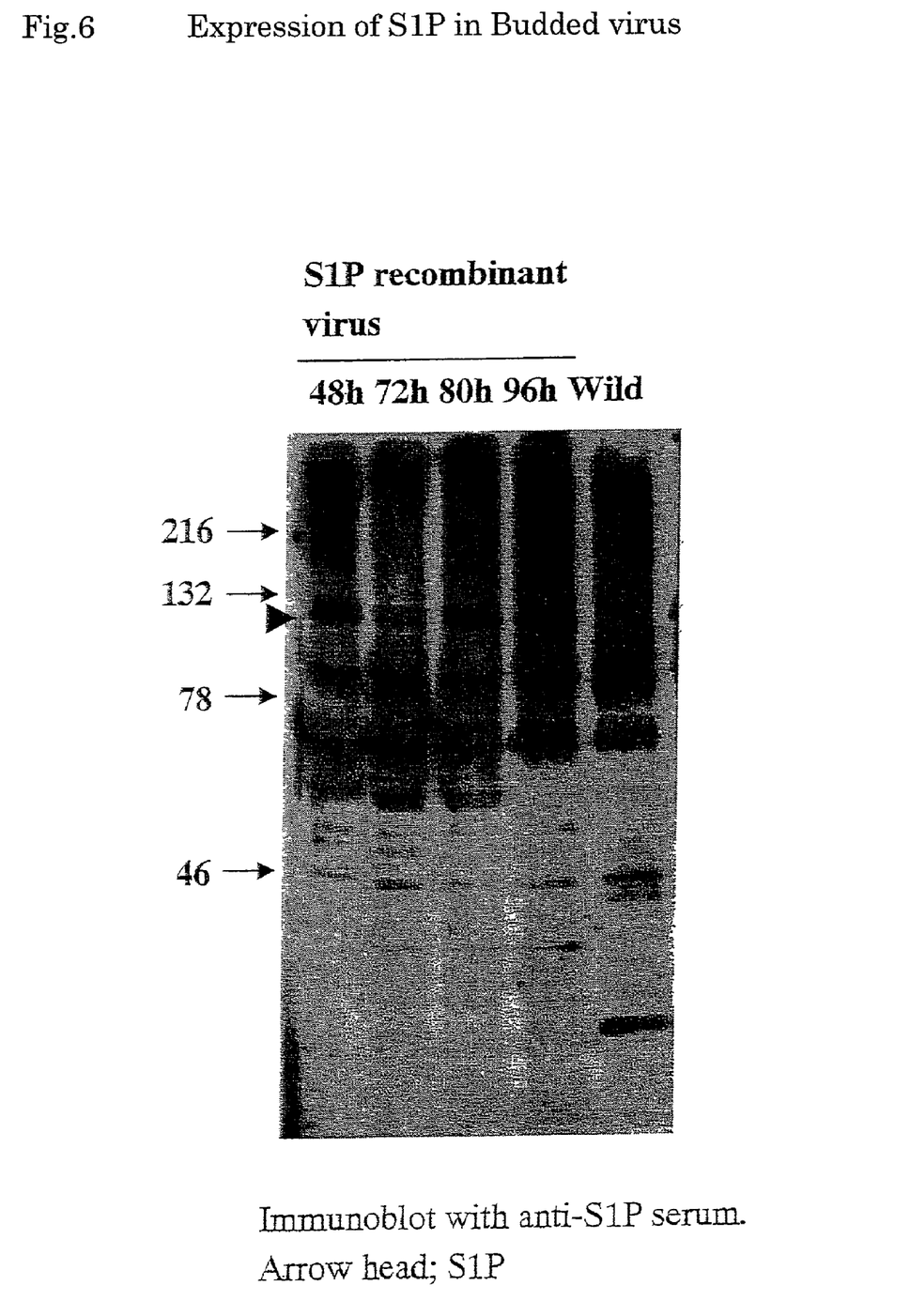
FIG. 6 is an illustration showing the result of expression of S1P in the budded virus.
Figure 7:
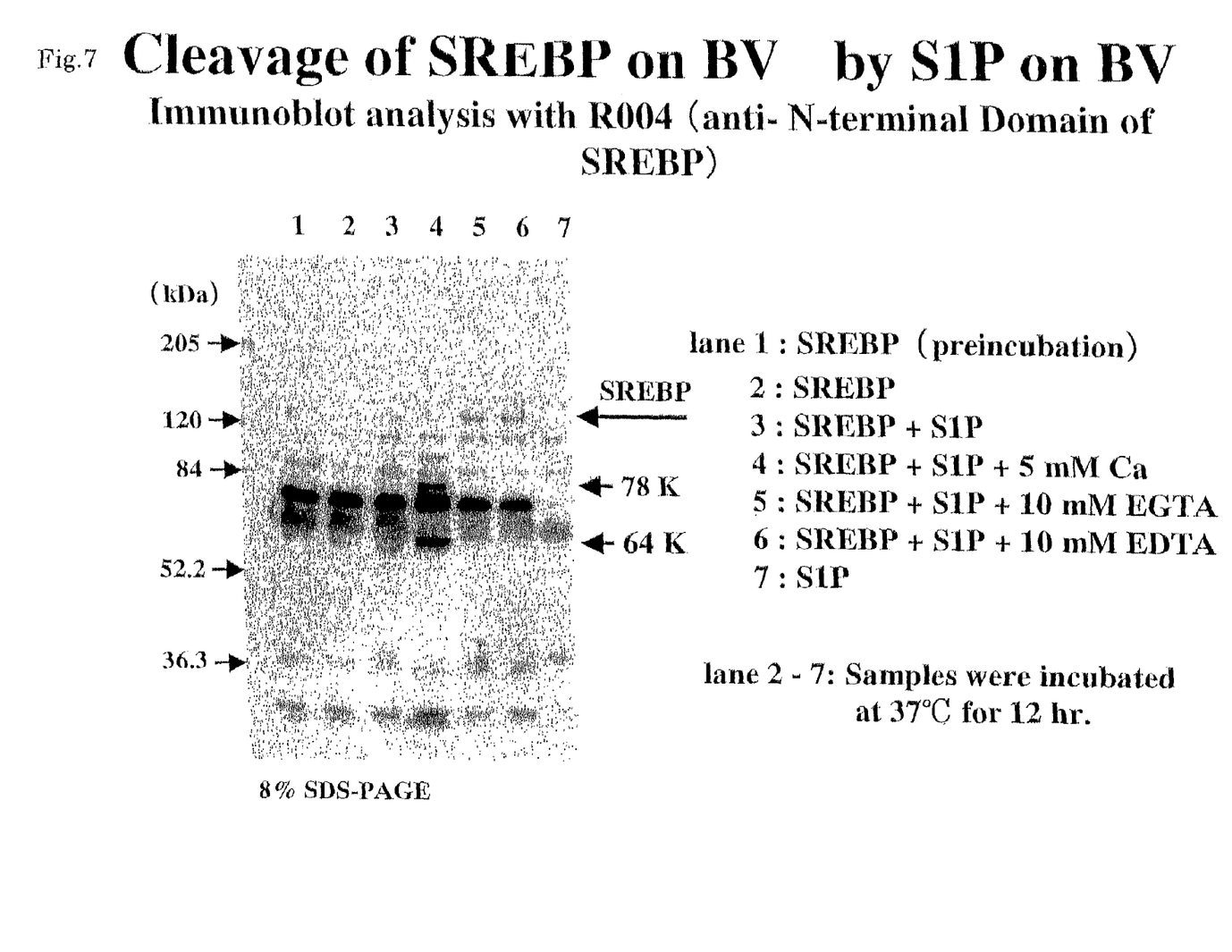
FIG. 7 is an illustration showing cleavage of SREBP on the budded virus by S1P on the budded virus.

(7) Immunization of Mice $1 \times 10^9$ cells/500 ml of Sf9 suspension cells were infected with SREBP2 recombinant viruses at MOI 5. 72 hours later, budded baculoviruses (BV) were suspended and recovered by ultra-centrifugation in 4 ml of phosphate buffered saline (PBS). Mice were divided into three groups, each of which is of 2 mice, and immunized with virus solutions of 0.1 μl, 1 μl, and 10 μl, respectively. It was confirmed that anti-sera is produced upon two times of immunization (FIG. 5).

Example 2

Expression of S1P

S1P is a protease of one-transmembrane type which cleaves a precursor of sterol regulatory element binding protein SREBP (Sakai J, Rawson R B, Espenshade P J, Cheng D, Seegmiller A C, Goldstein J L, Brown M S., Mol Cell. 1998 October; 2(4): 505–14., Molecular identification of the sterol-regulated luminal protease that cleaves SREBPs and controls lipid composition of animal cells). S1P recognizes the RSVL sequence in the ER intraluminar loop of SREBP and cleaves it at the carboxyl end of a leucine residue. After synthesis in ER as a pro form (148 kd) consisting of 1052 amino acids, the signal peptide is cut off to produce S1P type A(120 kd). Subsequently, S1P type A is transported to Golgi body and is activated by auto-decomposition, resulting in S1P type B (106 kd) or type C (98 kd) (Espenshade P J, Cheng D, Goldstein J L, Brown M S., J Biol Chem. 1999 August 6; 274(32): 22795–804., Autocatalytic processing of site-1 protease removes propeptide and permits cleavage of sterol regulatory element-binding proteins). S1P has been also reported as a processing enzyme of brain-derived neurotrophic factor (BDNF) (Seidah N G, Mowla S J, Hamelin J, Mamarbachi A M, Benjannet S, Toure B B, Basak A, Munzer J S, Marcinkiewicz J, Zhong M, Barale J C, Lazure C, Murphy R A, Chretien M, Marcinkiewicz M., Proc. Natl. Acad. Sci. U.S.A. 1999 February 16; 96(4): 1321–6. Mammalian subtilisin/kexin isozyme SKI-1: A widely expressed proprotein convertase with a unique cleavage specificity and cellular localization).

As in Example 1, a vector was constructed by integrating human S1P cDNA (KIAA0091, Kazusa DNA Research Institute) into pBlueBachis2™. Sf9 cells were co-infected with this vector and ApMNPV DNA (BAC-N-BLUE™, Invitrogen), thereby obtaining recombinant viruses. High Five™ cells (Invitrogen) were suspension- and sub-cultured in Express Five SFM (Gibco) supplemented with 16.5 mM L-glutamine.

High Five™ cells (Invitrogen) were infected with the recombinant viruses at MOI 5, and then extracellular budded viruses (BV) were prepared as described in Example 1. A partial amino acid sequence 589–604 of human S1P was synthesized, conjugated to Keyhole Limpet Hemocyanin, and used to immunize a rabbit, thereby obtaining anti-serum R03.

Expression of S1P in BV was examined using the thus prepared BV by immunoblotting with R03. As in Example 1, S1P was recovered in the culture supernatant centrifugation fraction (BV fraction) on and after 48 hours of culturing (FIG. 6).

Example 3

Measurement of Membrane Protease Activity

S1P is an enzyme which cleaves at almost the center of the 125 kd precursor protein of SREBP as described in Example 2. The cleavage site contains an RXXL sequence. Cleavage occurs at the carboxyl end of the leucine (L) residue. In SREBP2, the cleavage site of S1P which is RSVL is localized between two transmembrane sites at almost the center of the loop protruding into ER cavity. The cleavage is thought to occur in Golgi cavity when cholesterol content of cells decreases (Brown M S, Goldstein J L., Proc. Natl. Acad. Sci. USA, 1999 September; 96: 11041–11240., A proteolytic pathway that controls the cholesterol content of membranes, cells, and blood).

If SREBP2 was expressed in the extracellular virus (BV) envelope in the correct orientation in Example 1, this would suggest that the cleavage site of SREBP2 was orientated towards the outside the virus. Similarly in Example 2, if S1P was expressed in BV in the correct orientation, this would suggest that the active site is located on the outside of the virus. To confirm if cleavage of SREBP2 by S1P occurred, both the virus solutions were mixed and incubated.

(Methods and Results)

Measurement of SREBP2 Cleavage Activity of S1P

Sf9 cells were infected with recombinant viruses of S1P or SREBP at MOI 5. 72 hours later, the BV fraction was recovered by centrifugation as in Examples 1 and 2, and then suspended in TBS buffer (10 mM Tris, 150 mM NaCl, pH7.5). BV suspended in TBS was subjected to a protein determination with a protein determination kit (Bio-Rad). Reaction solutions of SREBP2-BV as a substrate and S1P-BV as an enzyme were prepared to have respective final concentrations of 10 μg per reaction solution. In addition, calcium ions required for activation of S1P were added to the reaction solution at a concentration, as calcium acetate, which enables to measure activity. Calcium, EDTA (pH7.4) and EGTA (pH7.4) were added to BV solution, and then added with TBS buffer (pH7.4) to a reaction volume of 20 μl, followed by incubation at 37° C. for 12 hours. Following reaction, the solution was subjected to heat treatment with 5×SDS sample buffer at 95° C. for 10 minutes, subjected to 8% SDS-PAGE and Western blot using rabbit anti-serum R004 against the amino terminal of SREBP2.

Measurement of SREBP2 Cleavage Activity of S1P

BV expressing SREBP or S1P was mixed, incubated at 37° C. for 12 hours, and then allowed to react in the presence of 5 mM calcium. Western blot analysis with anti-serum R004 detected two major bands that were thought to be degradation products of SREBP (FIG. 7). Molecular weights of the bands which were thought to be degradation products were approximately 78 kDa and 64 kDa as calculated based on protein mobility (Rf value). The molecular weight of 64 kDa coincided with that of a degradation product (N terminus) resulting from cleavage of SREBP-2 by S1P as reported. Further, this degradation was completely inhibited by 10 mM EDTA. These results agreed with the S1P properties that have been reported (Toure, B. B., Munzer, J. S., Basak, A., Benjannet, S., Rochemont, J., Lazure, C., Chretien, M. and Seidah, N. G. (2000): Biosynthesis and Enzymatic Characterization of Human SKI-1/S1P and the processing of its inhibitory prosegment. J. Biol. Chem. 275, 2349–2358). However, a degradation product of 78 kDa has not been reported. Further purification and analysis are needed to know whether another cleavage site is present or this degradation is observed only in vitro.

Example 4

Expression of SCAP and Co-expression of SREBP2 and SCAP

SCAP (SREBP cleavage activating protein) is a membrane protein of eight-transmembrane type which has a sterol sensor domain (SSD), and is present in ER membrane while forming a hetero-dimer with SREBP (Loisel T P, Ansanay H, St-Onge S, Gay B, Boulanger P, Strosberg A D, Marullo S, Bouvier M., Nat. Biotechnol. 1997 November; 15(12): 1300–4., Recovery of homogeneous and functional beta 2-adrenergic receptors from extracellular baculovirus particles). SSD senses a decrease in cholesterol level and guides SREBP towards the Golgi body where S1P is distributed, by an unknown mechanism (DeBose-Boyd R A, Brown M S, Li W P, Nohturfft A, Goldstein J L, Espenshade P J., Cell. 1999 December 23; 99(7)703–12., Transport-dependent proteolysis of SREBP: relocation of site-1 protease from Golgi to ER obviates the need for SREBP transport to Golgi). As described above, SCAP is known as an activator which activates a transport of SREBP or a cleavage enzyme depending on cholesterol.

Expression of SCAP

Figure 8:
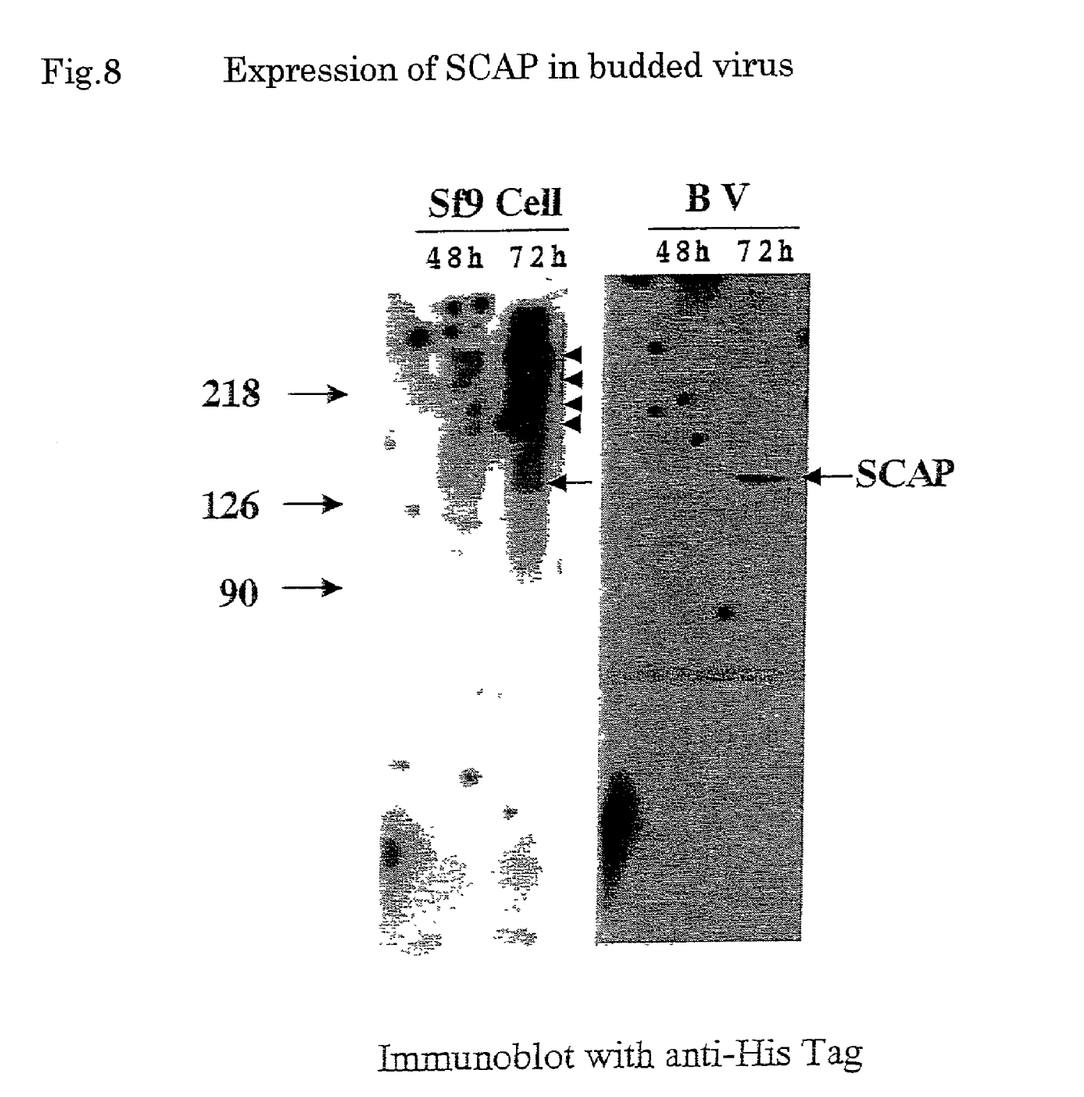
FIG. 8 is an illustration showing the result of expression of SCAP in the budded virus.

A vector was constructed by integrating a human SCAPcDNA (KIAA 0199, Kazusa DNA Research Institute) into pBlueBachis2™ (Invitrogen). Sf9 cells were co-infected with this vector and ApMNPV DNA (BAC-N-BLUE™, Invitrogen), thereby obtaining recombinant viruses. Sf9 cells were infected with the recombinant viruses at MOI5 as in Example 1. Immunoblotting with an antibody against His-tag (Qiagen) revealed that SCAP expressed in Sf9 cells aggregated but SCAP expressed in BV showed a correct electrophoretic mobility(FIG. 8).

Co-expression of SREBP2 and SCAP

SREBP2 and SCAP interact with each other at their carboxyl termini to form a hetero-dimer. This complex has been thought to be important in controlling cholesterol (Sakai J, Nohturfft A, Cheng D, Ho Y K, Brown M S, Goldstein J L., J. Biol. Chem. 1997 August 8; 272(32): 20213–21., Identification of complexes between the COOH-terminal domains of sterol regulatory element-binding proteins (SREBPs) and SREBP cleavage-activating protein).

Sf9 cells were co-infected at MOI5 with the recombinant virus of SREBP2 and that of SCAP prepared in Example 1. 72 hours later, BV was recovered from 200 ml of the culture supernatant and suspended in 4 ml of TBS. 1 ml of the suspension was added with lyso-phosphatidylcholine at a concentration of 1% (Sigma) and then treated at room temperature for 2 hours in the same manner as in the solubilization of SREBP2 in Example 1. Then, centrifugation was performed at 10,000 g for 10 minutes at 4° C. to separate and recover the supernatant and the precipitate. The supernatant was a soluble fraction and the precipitate was made into pellet after solubilization. 500 µl of the soluble fraction was dispensed into each of two 1.5 ml tubes, to which 30 µl of 1C6 affinity sepharose or 30 µl of Ni-NTA agarose (Qiagen) was added. The mixture was stirred at 4° C. for 16 hours. Each tube was centrifuged at 300 g for 3 minutes, resulting in the supernatant as an immunoprecipitation supernatant and the precipitate as an immunoprecipitation pellet. The immunoprecipitation supernatant (200 µl) was subjected to acetone precipitation (5 volumes of acetone was added, allowed to stand at −20° C. for 30 minutes, and then centrifuged at 3,000 g for 20 minutes). The product was suspended in 80 µl of a dissolution buffer (10 mM Tris-HCl, pH6.8, 100 mM NaCl, 1% SDS, 1 mM sodium EDTA, 1 mM sodium EGTA), to which 20 µl of 5×SDS sample buffer was added, followed by heat treatment at 95° C. for 5 minutes, thereby obtaining a sample for SDS-PAGE (Lanes 4 and 5 of FIG. 9).

The immunoprecipitation pellet was washed by suspending in 500 µl of TBS containing 0.5% lyso-phosphatidyl-choline, and stirring at 4° C. for 16 hours. This was a first washing. Second and third washings were performed by adding the same amount of buffer and stirring for 1 hour. The supernatant was removed by centrifugation at 300 g for 3 minutes. After washing, the immunoprecipitation pellet was suspended in 100 µl of a 2×SDS sample buffer (60 mM Tris-HCl, pH6.8, 10% β-mercaptoethanol, 6% SDS, 10% glycerol, 0.008% bromophenolblue). Following heat treatment at 95° C. for 10 minutes, centrifugation was performed at 1000 g for 10 minutes, thereby recovering the supernatant as a sample for SDS-PAGE (lanes 6 and 7 of FIG. 9).

Figure 9:
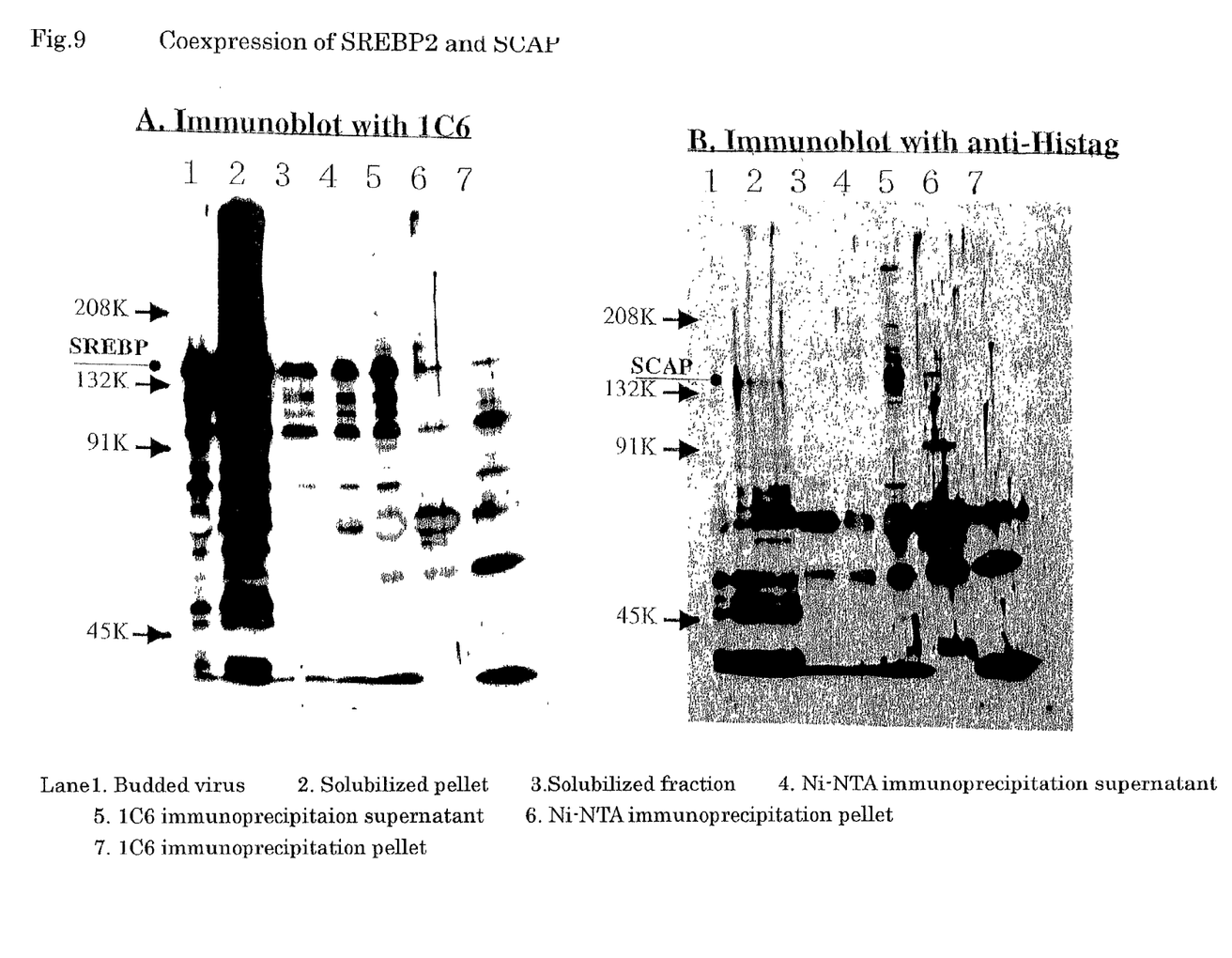
FIG. 9 is an illustration showing the result of co-expression of SREBP2 and SCAP in the budded virus.

SDS-gel electrophoresis and immunoblot staining were performed in the same manner as in Example 1. Each sample for SDS-PAGE was subjected to gel electrophoresis on 7.5% SDS-PAGE, transferred to a nitrocellulose membrane at 70V for 2 hours, and then Western blot was performed. SREBP and SCAP were detected with the antibody 1C6 or the antibody against His-tag. Ni-NTA Agarose resulted in co-precipitation of SREBP and SCAP, suggesting that SREBP and SCAP formed complexes also in the baculovirus expression system (FIG. 9). In the 1C6 affinity Sepharose, only SREBP which formed no complex was precipitated, suggesting that 1C6 became incapable of recognizing an antigen site because of the formation of a complex of SREBP and SCAP.

INDUSTRIAL APPLICABILITY

Unlike membrane proteins which are recovered from Sf9 cell nuclei together with many degradation products, a highly stable endoplasmic reticulum membrane protein can be recovered in the viral envelope and recovered as a single band according to a method of the present invention, which expresses, in budded baculovirus, a protein selected from a membrane-bound enzyme, a substrate of the membrane-bound enzyme, a membrane-bound enzyme activator, a membrane-bound transport protein, a channel protein, a membrane structural protein, a protein involved in adhesion, a protein involved in antigen presentation, or a protein involved in formation of high dimensional structure of a protein. Although preparation of membrane proteins (particularly endoplasmic reticulum membrane proteins) is generally difficult because they are exposed to degradation enzymes such as lysozome when separating from a cell, membrane proteins expressed by the method of the present invention in extracellular viral envelopes can be easily prepared and possess good stability. The method of the present invention can be utilized for producing specific antibodies, purifying membrane proteins, measuring interaction between membrane proteins, and the like.

What is claimed is:

1. A method for recovering a budded baculovirus expressing an intracellular organelle membrane-bound protein selected from a membrane-bound enzyme, a substrate of the membrane-bound enzyme, a membrane-bound enzyme activator, a membrane-bound transport protein, a channel protein, a membrane structural protein, or a protein involved in formation of high dimensional structure of a protein comprising culturing a host infected with at least one recombinant baculovirus which contains a gene encoding said protein, expressing said protein in said infected host allowing baculovirus produced in said host to bud and be released from said host with said expressed protein being in the envelope of said budded baculovirus, and separating the budded baculovirus.

2. A method for preparing an intracellular organelle membrane-bound protein which comprises:

culturing a host infected with a recombinant baculovirus which contains a gene encoding protein selected from a membrane-bound enzyme, a substrate of the membrane-bound enzyme, a membrane-bound enzyme activator, a membrane-bound transport protein, a channel protein, a membrane structural protein, or a protein involved in formation of high dimensional structure of a protein;

recovering a budded baculovirus released from said host; and recovering the protein expressed in said infected host allowing baculovirus produced in said host to bud and be released from said host with said expressed protein being in the envelope of said budded baculovirus.

3. The method of claim 1 wherein the protein selected from a membrane-bound enzyme, a substrate of the membrane-bound enzyme, a membrane-bound enzyme activator, a membrane-bound transport protein, a channel protein, a membrane structural protein, or a protein involved in formation of high dimensional structure of a protein is a membrane-bound protein of a cell organelle.

4. The method of claim 2 wherein the protein selected from a membrane-bound enzyme, a substrate of the membrane-bound enzyme, a membrane-bound enzyme activator, a membrane-bound transport protein, a channel protein, a membrane structural protein, or a protein involved in formation of high dimensional structure of a protein is a membrane-bound protein of a cell organelle.

5. The method of claim 1 wherein the protein selected from a membrane-bound enzyme, a substrate of the membrane-bound enzyme, a membrane-bound enzyme activator, a membrane-bound transport protein, a channel protein, a membrane structural protein, or a protein involved in formation of high dimensional structure of a protein is SREBP2, HMG-CoA reductase, S1P, or SREBP cleavage activating protein.

6. The method of claim 2 wherein the protein selected from a membrane-bound enzyme, a substrate of the membrane-bound enzyme, a membrane-bound enzyme activator, a membrane-bound transport protein, a channel protein, a membrane structural protein, or a protein involved in formation of high dimensional structure of a protein is SREBP2, HMG-CoA reductase, S1P, or SREBP cleavage activating protein.

7. The method of claim 1 wherein the host is an insect cell or an insect larva.

8. The method of claim 2 wherein the host is an insect cell or an insect larva.

9. The method of claim 1, wherein the protein is an Endoplasmic Reticulum-associated protein.

10. The method of claim 1, wherein the protein is an Golgi Apparatus-associated protein.

11. The method of claim 2, wherein the protein is an Endoplasmic Reticulum-associated protein.

12. The method of claim 2, wherein the protein is an Golgi Apparatus-associated protein.

13. The method of claim 1, wherein the protein is SREBP2, HMG-CoA reductase, S1P, or SREBP cleavage activating protein.

14. The method of claim 2, wherein the protein is SREBP2, HMG-CoA reductase, S1P, or SREBP cleavage activating protein.

15. A method for recovering a budded baculovirus expressing a non-receptor protein selected from a membrane-bound enzyme, a substrate of the membrane-bound enzyme, a membrane-bound enzyme activator, a membrane-bound transport protein, a channel protein, a membrane structural protein, or a protein involved in formation of high dimensional structure of a protein comprising culturing a host infected with at least one recombinant baculovirus which contains a gene encoding said protein, expressing said protein in said infected host allowing baculovirus produced in said host to bud and be released from said host with said expressed protein being in the envelope of said budded baculovirus, and separating the budded baculovirus.

16. The method of claim 15, wherein the protein is an Endoplasmic Reticulum-associated protein.

17. The method of claim 15, wherein the protein is an Golgi Apparatus-associated protein.

18. The method of claim 15, wherein the protein is SREBP2, HMG-CoA reductase, S1P, or SREBP cleavage activating protein.

19. A method for preparing a non-receptor protein which comprises:

culturing a host infected with a recombinant baculovirus which contains a gene encoding protein selected from a membrane-bound enzyme, a substrate of the membrane-bound enzyme, a membrane-bound enzyme activator, a membrane-bound transport protein, a channel protein, a protein involved in antigen presentation, or a protein involved in formation of high dimensional structure of a protein;

recovering a budded baculovirus released from said host; and recovering the protein expressed in said infected host allowing baculovirus produced in said host to bud and be released from said host with said expressed protein being in the envelope of said budded baculovirus.

20. The method of claim 19, wherein the protein is an Endoplasmic Reticulum-associated protein.

21. The method of claim 19, wherein the protein is an Golgi Apparatus-associated protein.

22. The method of claim 19, wherein the protein is SREBP2, HMG-CoA reductase, S1P, or SREBP cleavage activating protein.

* * * * *